(12) United States Patent
Chan et al.

(10) Patent No.: US 9,242,953 B2
(45) Date of Patent: Jan. 26, 2016

(54) PROCESS FOR PREPARING DRONEDARONE AND SALTS THEREOF

(71) Applicant: Gilead Sciences, Inc., Foster City, CA (US)

(72) Inventors: Johann Chan, San Mateo, CA (US); Justin Vitale, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/468,993

(22) Filed: Aug. 26, 2014

(65) Prior Publication Data

US 2015/0065734 A1    Mar. 5, 2015

Related U.S. Application Data

(60) Provisional application No. 61/903,285, filed on Nov. 12, 2013, provisional application No. 61/870,632, filed on Aug. 27, 2013.

(51) Int. Cl.
| | | |
|---|---|---|
| *C07D 307/00* | (2006.01) | |
| *C07D 307/80* | (2006.01) | |
| *C07D 307/83* | (2006.01) | |
| *C07D 307/85* | (2006.01) | |
| *C07D 307/81* | (2006.01) | |

(52) U.S. Cl.
CPC ............ *C07D 307/80* (2013.01); *C07D 307/81* (2013.01); *C07D 307/83* (2013.01); *C07D 307/85* (2013.01)

(58) Field of Classification Search
CPC ... C07D 307/81; C07D 307/83; C07D 307/85
USPC .................................................. 549/468, 466
See application file for complete search history.

(56) References Cited

U.S. PATENT DOCUMENTS 5,223,510 A *   6/1993  Gubin et al. ................... 514/299
6,828,448 B2 * 12/2004  Fino et al. ..................... 549/471

FOREIGN PATENT DOCUMENTS

| EP | 2617718 A1 | 7/2013 | |
|---|---|---|---|
| EP | 2617718 A1 * | 7/2013 | .................. 549/471 |
| WO | WO-2011099010 A1 | 8/2011 | |
| WO | WO 2011107705 A1 * | 9/2011 | .................. 549/471 |
| WO | WO 2011158050 A1 * | 12/2011 | .................. 549/471 |

OTHER PUBLICATIONS

Banning et al. (2013) "Formal Substitution of Bromocylopropanes with Nitrogen Nucleophiles" *The Journal of Organic Chemistry*78(15):7601-7616.

Larghi et al. (1997) "Preparation of N-Benzylsulfonamido-1,2-Dihydroisoquinolines and Their Reaction with Raney Nickel. A Mild, New Synthesis of Isoquinolines" *Tetrandron Letters, Peroarnon, GB* 38(18): 3159-3162.

Yao et al. (2009) "Iron-Catalyzed Amidation of Alkynyl Bromides: A Facile Route for the Preparation of Ynamides" *The Journal of Organic Chemistry* 74(12: 4630-4633.

International Search Report for PCT/US2014/052692, International filing date Aug. 26, 2014, mailed Oct. 6, 2014.

* cited by examiner

*Primary Examiner* — Andrew D Kosar
*Assistant Examiner* — Raymond Covington
(74) *Attorney, Agent, or Firm* — Francis O. Ginah

(57) ABSTRACT

The present disclosure relates to processes for preparing dronedarone or pharmaceutically acceptable salts thereof.

6 Claims, No Drawings

PROCESS FOR PREPARING DRONEDARONE AND SALTS THEREOF

CROSS REFERENCE TO RELATED APPLICATIONS

This application claims the benefit under 35 U.S.C. §119(e) to U.S. Provisional Application Ser. No. 61/870,632, filed on Aug. 27, 2013, and U.S. Provisional Application Ser. No. 61/903,285, filed Nov. 12, 2013, the entirety of which is incorporated herein by reference.

FIELD OF THE INVENTION

The present invention relates to a process for preparing dronedarone.

BACKGROUND

Atrial fibrillation (AF) is the most prevalent arrhythmia, the incidence of which increases with age. It is estimated that 8% of all people over the age of 80 experience this type of abnormal heart rhythm and AF accounts for one-third of hospital admissions for cardiac rhythm disturbances. Over 2.2 million people are believed to have AF in the Unites States alone. Fuster, et al *Circulation* 2006 114 (7): e257-354. Although atrial fibrillation is often asymptomatic it may cause palpitations or chest pain. Prolonged atrial fibrillation often results in the development of congestive heart failure and/or stroke. Heart failure develops as the heart attempts to compensate for the reduced cardiac efficiency while stroke may occur when thrombi form in the atria, pass into the blood stream and lodge in the brain. Pulmonary emboli may also develop in this manner.

U.S. Pat. No. 5,223,510 discloses alkylaminoalkyl derivatives of benzofuran, benzothiophene, indole and indolizine, processes for their preparation and compositions containing them. WO 2013/014480 discloses a process for manufacturing dronedarone comprising reduction of the compound of formula (II) to the compound of formula (I) as shown below:

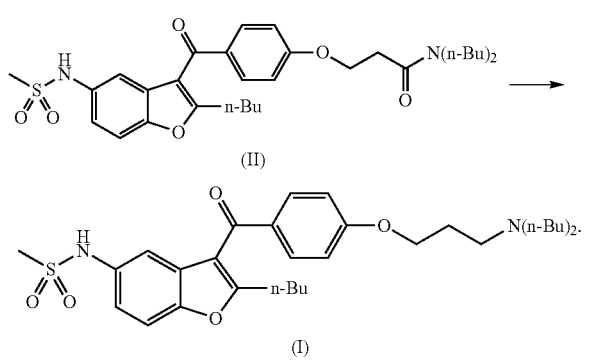

WO 2012/127174 discloses a process involving a Fries rearrangement converting, for example, the compound of formula (8) to the compound of formula (9) followed by coupling of the compound of formula (9) and dibutylamino propyl chloride to afford the compound of formula (I).

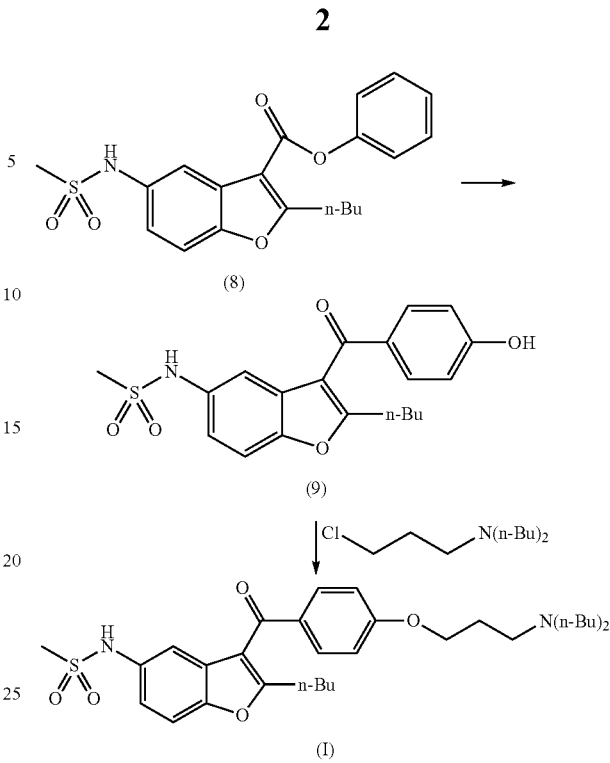

European patent application EP2617718A1 discloses processes for preparing dronedarone comprising reacting the intermediate

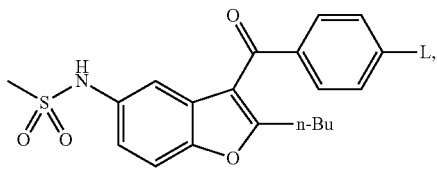

where L is a leaving group with dibutylaminopropanol.

The above disclosures notwithstanding, there remains a need for alternate or improved processes for preparing dronedarone.

SUMMARY OF THE DISCLOSURE

The present disclosure provides a process for making dronedarone of formula I

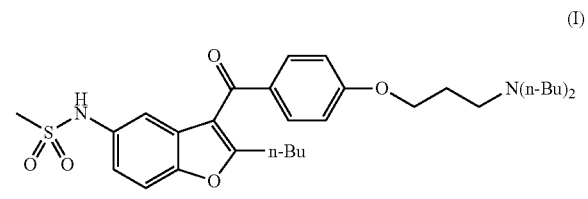

or a pharmaceutically acceptable salt thereof, comprising the steps of:

a. reacting the compound of formula (1) with the compound of formula (2) in the presence of a Lewis acid and a suitable solvent to form the compound of formula (3) as shown below:

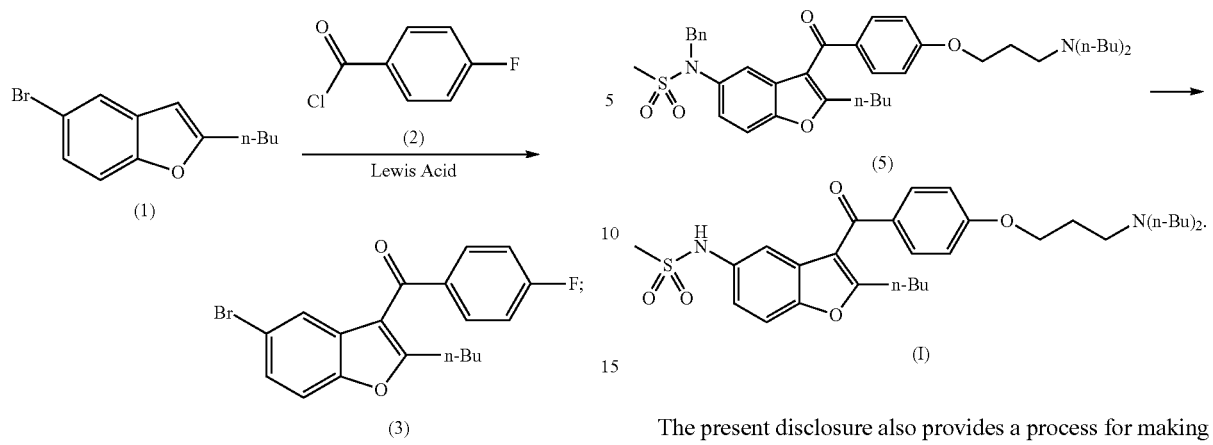

b. reacting the compound of formula (3) with N-benzyl-methanesulfonamide (MeSO$_2$NHBn) in the presence of a suitable catalyst and a suitable solvent to form the compound of formula (4) as shown below:

c. reacting the compound of formula (4) with dibutylaminopropanol in the presence of a suitable base and a suitable solvent to form the compound of formula (5) as shown below:

d. reacting the compound of formula (5) with a suitable deprotecting agent to form the compound of formula (I) as shown below:

The present disclosure also provides a process for making dronedarone acid addition salt comprising the steps of:

a. reacting the compound of formula (1) with the compound of formula (2) in the presence of a Lewis acid and a suitable solvent to form the compound of formula (3) as shown below:

b. reacting the compound of formula (3) with N-benzyl-methanesulfonamide (CH$_3$SO$_2$NHBn) in the presence of a suitable catalyst and a suitable solvent to form the compound of formula (4) as shown below:

-continued

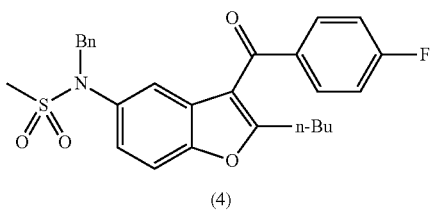

(4)

c. reacting the compound of formula (4) with dibutylaminopropanol in the presence of a suitable base and a suitable solvent to form the compound of formula (5) as shown below:

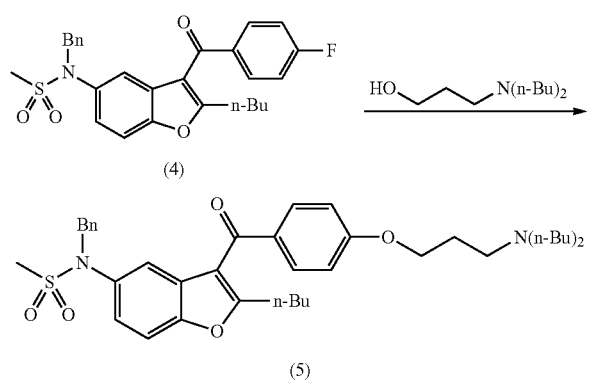

d. reacting the compound of formula (5) with a suitable deprotecting agent to form the compound of formula (I) as shown below:

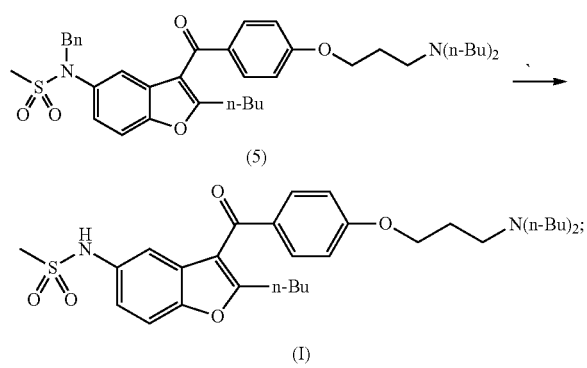

and e. reacting the compound of formula (I) with a suitable acid (HA) and a suitable solvent to afford the acid salt of the compound of formula (I) as shown below:

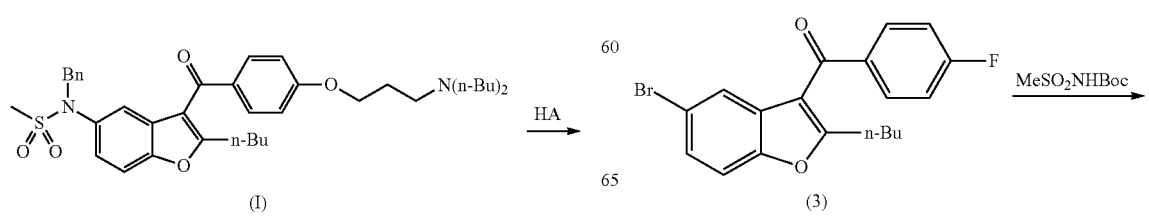

-continued

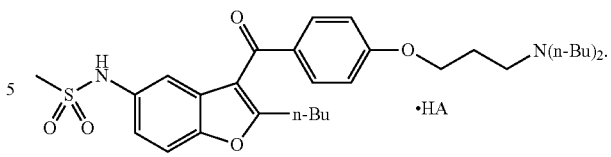

The present disclosure also provides a process for making dronedarone of formula (I)

(I)

or a pharmaceutically acceptable salt thereof, comprising the steps of:

a. reacting the compound of formula (1) with the compound of formula (2) in the presence of a Lewis acid and a suitable solvent to form the compound of formula (3) as shown below

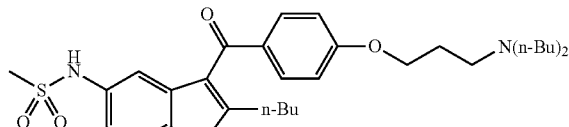

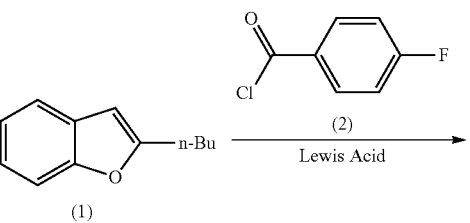

(3)

b. reacting the compound of formula (3) with Boc-protected methanesulfonamide and a suitable catalyst and a suitable solvent to afford the Boc-protected compound of formula (6) as shown below:

-continued

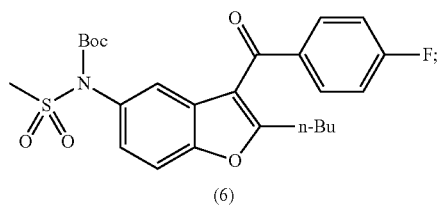

(6)

c. reacting compound of formula (6) with dibutylaminopropanol, a suitable base and a suitable solvent to afford the compound of formula (7) as shown below:

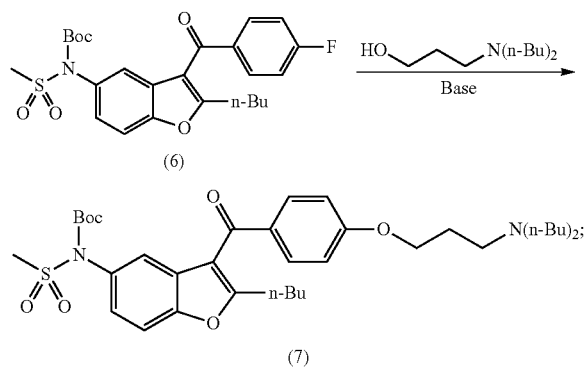

d. reacting the compound of formula (7) with a suitable acid and a suitable solvent to afford the compound of formula (I) as shown below:

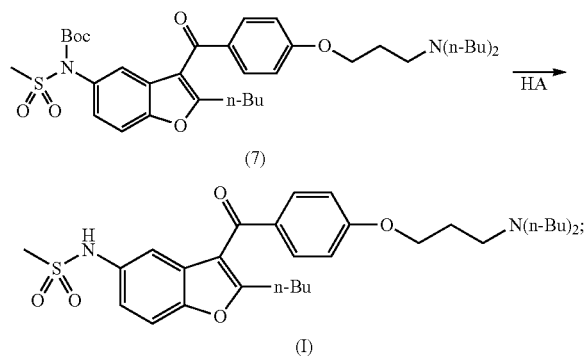

and e. optionally reacting the compound of formula (7) with a sufficient amount of a suitable acid to form the acid salt of the compound of formula (I) as shown below:

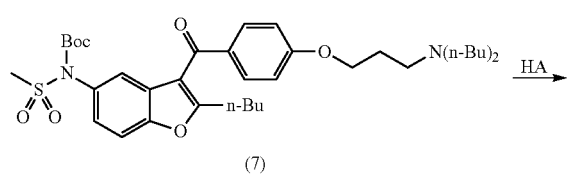

-continued

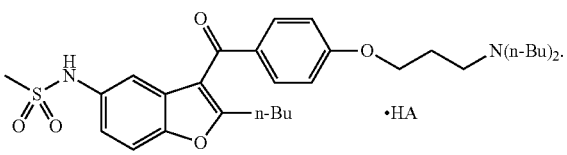

One advantage of the present disclosure is that it obviates certain mutagenic impurities observed with the process disclosed in U.S. Pat. No. 5,223,510. One of skill in the art is aware by virtue of the present disclosure that other protecting groups may be used in place of the protecting groups (benzyl or Boc) disclosed herein.

An object of the present disclosure is also the provision of intermediate compounds useful for making the compound of formula (I) or salts thereof. Thus, in one embodiment the present disclosure provides a compound of formula (4)

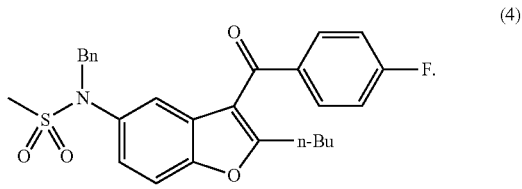

In another embodiment, the present disclosure provides a compound of formula (5)

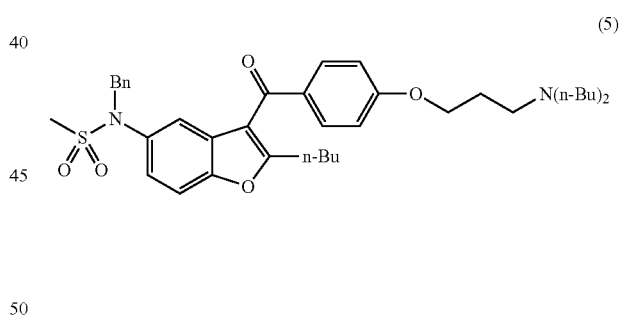

or a salt thereof.

In another embodiment the present disclosure provides a compound of formula (6)

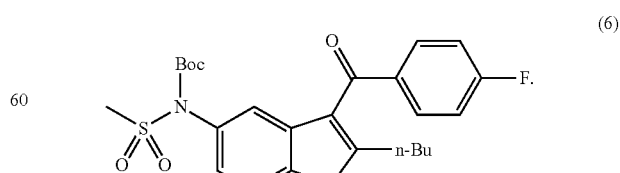

In yet another embodiment, the present disclosure provides a compound of formula (7)

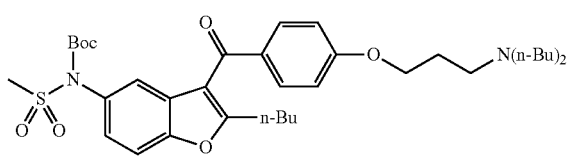

(7)

or a salt thereof.

DETAILED DESCRIPTION OF THE DISCLOSURE

Definitions and General Parameters

As used in the present specification, the following words and phrases are generally intended to have the meanings as set forth below, except to the extent that the context in which they are used indicates otherwise.

It is to be noted that as used herein and in the claims, the singular forms "a," "an" and "the" include plural referents unless the context clearly dictates otherwise. Thus, for example, reference to "a pharmaceutically acceptable carrier" in a composition includes two or more pharmaceutically acceptable carriers, and so forth.

"Dronedarone" is described in U.S. Pat. No. 5,223,510. Dronedarone refers to the chemical compound, N-(2-butyl-3-(4-(3-(dibutylamino)propoxy)benzoyl)benzofuran-5-yl) methanesulfonamide. The base form of dronedarone has the following chemical formula:

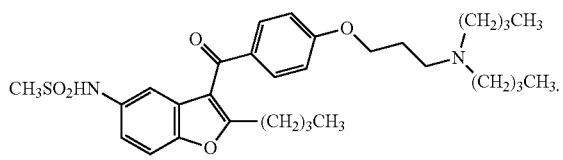

The term "deprotecting agent" as used herein refers to a reagent or reagent system (reagent(s), and solvent) useful for removing a protecting group. Deprotecting agents are acids, bases or reducing agents. For example, removal of the benzyl (Bn) group is generally accomplished by reduction (hydrogenolysis), while removal of carbamates (e.g. Boc group) is generally effected by use of acids (e.g. HCl, TFA, etc.) optionally with mild heating.

The term "suitable solvent" as used herein means a solvent that is useful for effecting the subject reaction. One of skill in the art is aware of the many solvents regarded as useful in the art for the purpose of the particular reaction. Suitable solvents are also exemplified by the solvents disclosed herein for the specific reaction.

The term "suitable base" as used means a base that is useful for effecting the subject reaction. One of skill in the art is aware of the many bases (organic and inorganic bases) regarded as useful in the art for the purpose of the particular reaction. Suitable bases are also exemplified by the bases disclosed herein for the specific reaction.

The term "suitable catalyst" as used means a catalyst that is useful for effecting the subject reaction. One of skill in the art is aware of the many catalysts regarded as useful in the art for the purpose of the particular reaction. Hydrogenation may be performed in the presence of palladium on carbon catalyst. Suitable catalysts are also exemplified by the catalysts disclosed herein for the specific reaction. The term suitable catalyst as used herein includes an appropriate ligand that may be necessary to effect or accelerate the action of the catalyst. One of ordinary skill in the art is aware that certain catalytic reactions, e.g. palladium catalyzed coupling reactions may require a ligand, e.g. triphenyl phosphine. Examples of ligands useful for catalytic reactions disclosed herein are provided in the experimental section below.

The term "suitable acid" as used means an acid that is useful for effecting the subject reaction. One of skill in the art is aware of the many acids (organic and inorganic acids) regarded as useful in the art for the purpose of the particular reaction. Suitable acids are also exemplified by the acids disclosed herein for the specific reaction.

A method for preparing the compound of formula (1)

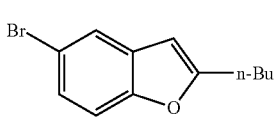

(1)

has been disclosed (see *Polish Journal of Applied Chemistry* 2002, 46, 21-29). The compound of formula (1) may also be prepared following additional procedures known to one of ordinary skill in the art.

The compound of formula (2)

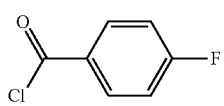

(2)

is available commercially.

The compound of formula (3)

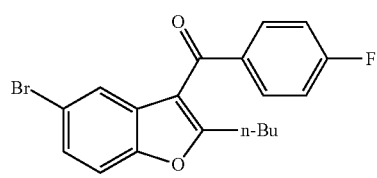

(3)

is prepared by reacting the compound of formula (1) with 4-fluorobenzoyl halide (2) in a Friedel-Crafts acylation procedure. A Lewis acid, such as aluminum trichloride ($AlCl_3$) is required to facilitate the reaction in polar aprotic solvents such as, for example, dichloromethane. The reaction may also be performed with catalysts such as zinc oxide or under microwave conditions without solvent (M. H. Sarvari, H. Sharghi, See Zinc Mediated Friedel-Crafts Acylation in Solvent-Free Conditions under Microwave Irradiation, *J. Org. Chem.* 2004, 69, 6953-6956). One of ordinary skill in the art is able to prepare the compound (3) without undue experimentation.

The compound of formula (4)

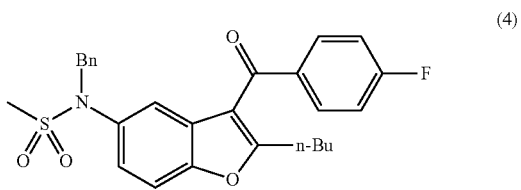

is prepared by reacting the compound of formula (3) with N-benzylmethanesulfonamide in the presence of a copper catalyst (e.g., CuI with an amine or a bis-amine ligand) under basic conditions. For example, approximately 5 mol % of CuI is sufficient to effect the reaction under basic conditions (e.g. in the presence of potassium carbonate or cesium carbonate in a solvent such as acetonitrile). The reaction may also be accomplished using palladium coupling methods known to one of ordinary skill in the art. Other bases, solvents and ligands may be used. However, for CuI catalyzed coupling, use of acetonitrile and potassium carbonate is preferred to achieve better yields of the coupled product (4). See Wang et al. *Tetrahedron Lett* 2012, 53, 7-10. The compound of formula (4) is a novel and useful intermediate for the preparation of the compound of formula (I) as disclosed herein. Thus, another aspect of the invention is the provision of the compound of formula (4).

The compound of formula (5)

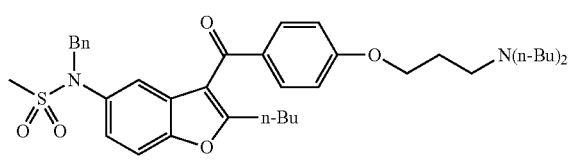

is prepared by reacting the compound of formula (4) with dibutylamino propanol using a suitable base and solvent. Dibutylaminopropanol is available commercially or may be prepared following procedures known to one of ordinary skill in the art. An example of a suitable base and solvent for the preparation of compound (5) is sodium t-butoxide and 1-methyl-2-pyrrolidinone (NMP).

The compound of formula (I)

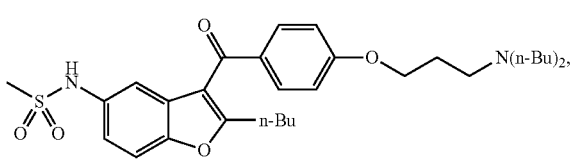

is prepared from the compound of formula (5) by, for example, hydrogenolysis in the presence of palladium on carbon and hydrogen gas or another appropriate hydrogen source and metal catalyst. One of skill in the art is aware of other procedures to remove benzyl protecting groups. For example, hydrogenation reactions to remove benzyl protecting groups are also commonly carried out with acidic additives and in protic solvents. Further, benzyl groups can also be removed by treatment with Lewis Acids and amines (e.g. AlCl$_3$/dimethyl-aniline).

The compound of formula (6)

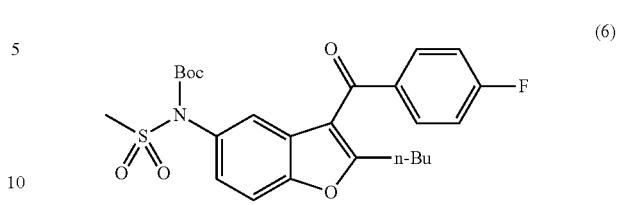

is formed by reacting the compound of formula (3) with Boc-protected methansulfonamide. Boc-protected methanesulfonamide (CH$_3$SO$_2$NHBoc) is commercially available. The reaction to form compound (6) is shown below:

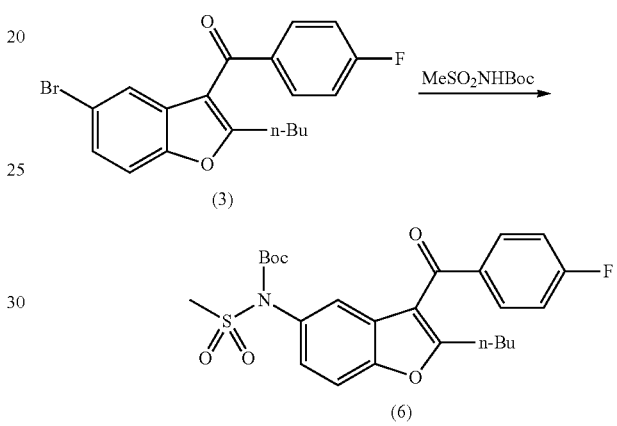

The reaction of compound (3) with N-boc-methansulfonamide may also be accomplished using a suitable catalyst. For example, approximately 5 mol % of CuI is typically sufficient to effect the reaction under basic conditions (e.g. in the presence of potassium carbonate or cesium carbonate in a solvent such as acetonitrile). The reaction may also be accomplished using palladium coupling methods known to one of ordinary skill in the art. Other bases, solvents, and ligands may be employed following procedures known to one of ordinary skill in the art. The compound of formula (6) is believed to be a novel and useful intermediate for the preparation of the compound of formula (I) as disclosed herein. Thus, another aspect of the invention is the provision of the compound of formula (6).

The compound of formula (7)

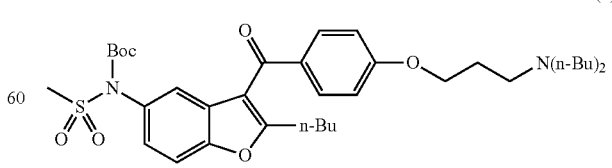

is prepared by reacting the compound of formula (6) with dibutylaminopropanol under basic conditions as shown below:

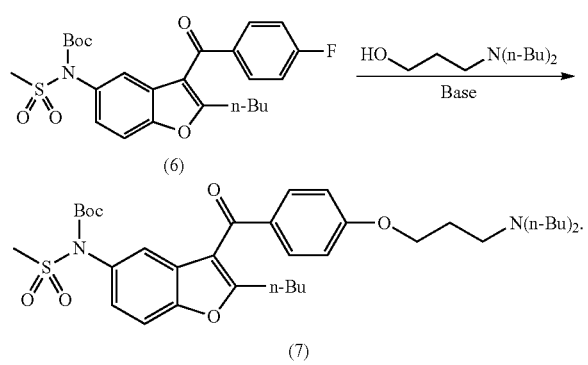

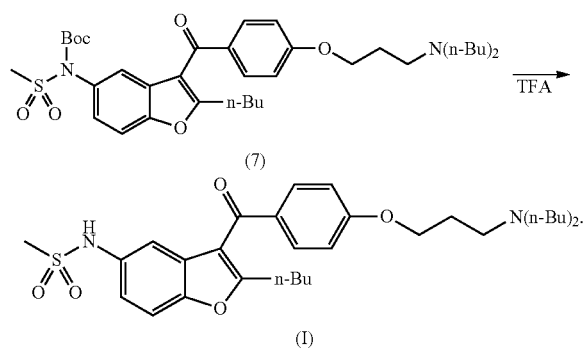

An example of a suitable base and solvent for the preparation of compound (7) is sodium tert-butoxide and 1-methyl-2-pyrrolidinone (NMP). Other reagents and reaction conditions are known to one of ordinary skill in the art. The compound of formula (7) is converted to the compound of formula (I) by removal of the Boc group using, for example, trifluoroacetic acid or aqueous HCl.

One of ordinary skill in the art is aware of procedures for removing protective groups. For example, reagents and procedures for adding or removing protecting groups are disclosed in *Protective Groups in Organic Synthesis*, Peter M. Wuts and Theodora W. Greene, 4th Edition, John Wiley Publishers.

The compound of formula (I) may be converted to a pharmaceutically acceptable salt by reaction with about a 1:1 molar equivalent of acid e.g. HCl (aqueous or gaseous) in a suitable solvent to afford the corresponding acid salt. One of ordinary skill in the art is able to form various acid salts of the compound of formula (I).

EXAMPLES

Dronedarone as used in this disclosure is well known in the art and may be prepared by following any one of many processes known to one of skill in the art including as disclosed in U.S. Pat. No. 5,223,510. Additionally, the abbreviations used throughout have the following meanings:

μM=micromolar
cm=centimeter
kg=kilogram
mA=milliamp
min=minute
mm=millimeter
mM=millimolar
Ms=Millisecond
1 vol=1 liter/Kg of limiting reagent

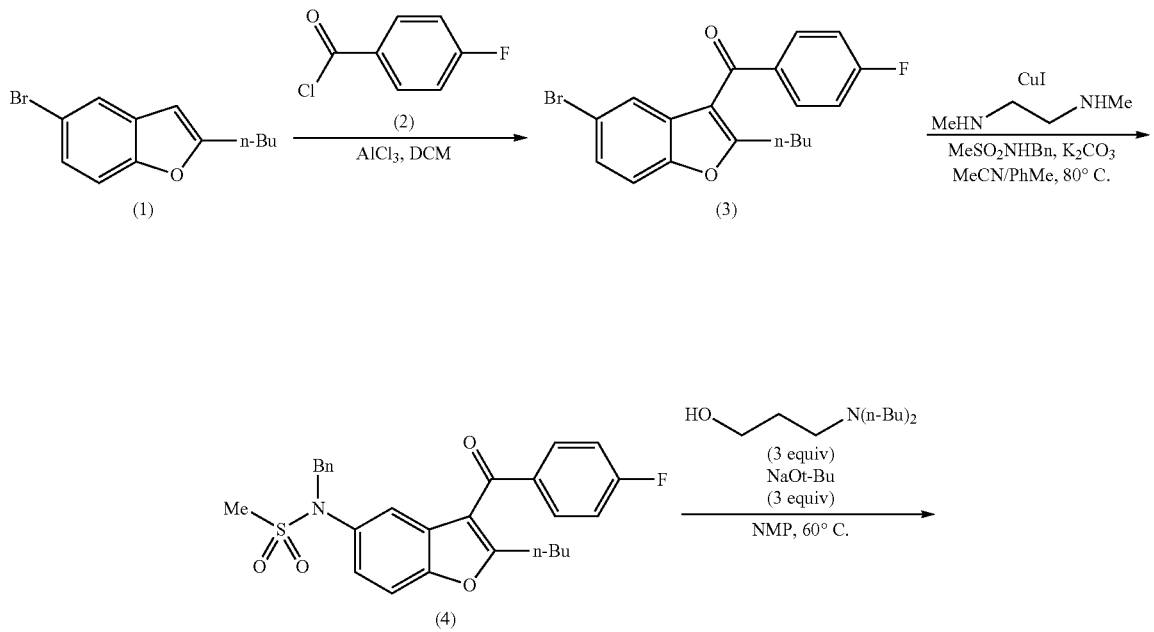

-continued

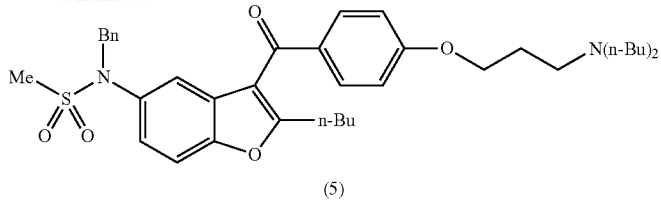

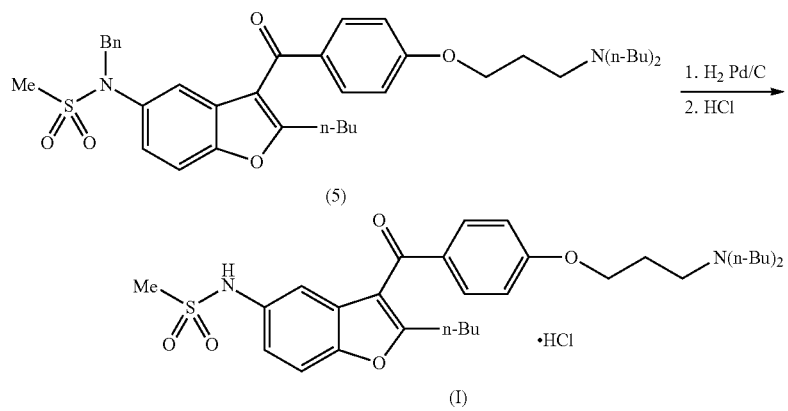

Example 1

I. Friedel Crafts Reaction of Compound (1) to Provide Compound (3)

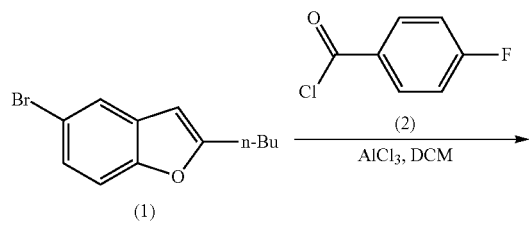

To a solution of compound (1) (1 equiv) and 4-fluorobenzoyl chloride (1.2 equiv) in CH$_2$Cl$_2$ (10 volumes) at ambient temperature is added AlCl$_3$ (0.5 equiv). The reaction is stirred at ambient temperature and then heated under reflux. The reaction mixture is diluted with CH$_2$Cl$_2$ (20 volumes) and quenched by the addition of ice-cold water (30 volumes). Following phase separation, the organic phase is dried over Na$_2$SO$_4$, filtered and concentrated under reduced pressure. The crude residue is purified by chromatography on silica gel (10 to 50% CH$_2$Cl$_2$ in heptane) to provide compound (3). $^1$H NMR (400 MHz, DMSO-d$_6$) δ ppm 7.82 (dd, J=8.6, 5.6 Hz, 2H), 7.62 (d, J=8.6 Hz, 1H) 7.43-7.53 (m, 2H), 7.37 (t, J=8.8 Hz, 2H), 2.72 (t, J=7.5 Hz, 2H), 1.71-1.49 (m, 2H), 1.29-1.09 (m, 2H), 0.74 (t, J=7.3 Hz, 3H); $^{19}$F NMR (376 MHz, DMSO-d$_6$) δ −106.39.

II. Cu-Catalyzed Sulfonamide Coupling of Compound (3) to Provide Compound (4)

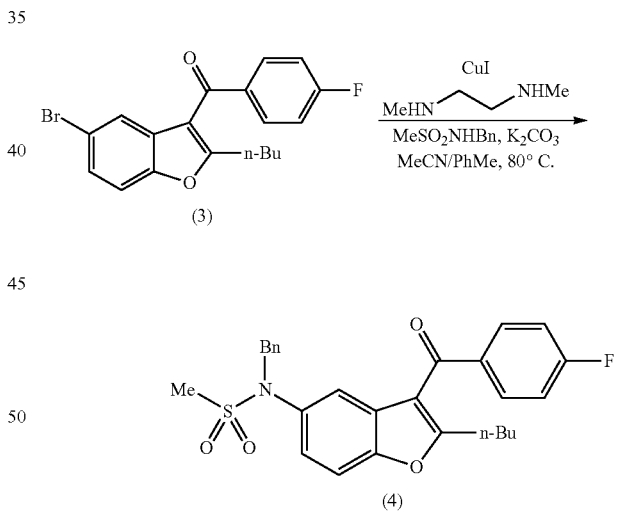

Compound (3) (1 equiv), N-benzylmethane sulfonamide (3 equiv), K$_2$CO$_3$ (3 equiv), CuI (0.5 equiv), acetonitrile (7 volumes) and toluene (7 volumes) are combined and the resulting mixture is sparged with N$_2$. N,N'-Dimethylethane-1,2-diamine (10 equiv.) is then added, and the reaction mixture is heated at about 80° C. for about 3 hours. The reaction mixture is cooled to ambient temperature and filtered through a pad of celite. The celite cake is rinsed with acetonitrile (13 volumes) and the filtrate is concentrated under reduced pressure. The residue is dissolved in isopropyl acetate (33 volumes), washed with aqueous HCl and 20% aqueous NaCl, dried over Na$_2$SO$_4$, filtered, and concentrated under reduced pressure. The crude residue is purified by chromatography on silica gel to afford compound (4).

III. Nucleophilic Aromatic Substitution of Compound (4) to Provide Compound (5)

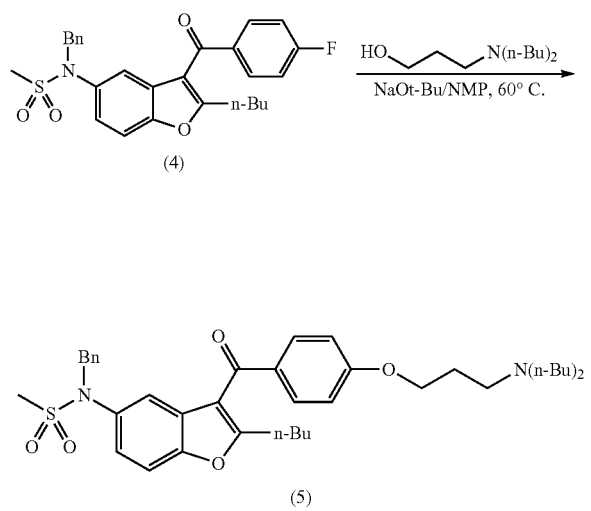

N-benzyl-N-(2-butyl-3-(4-fluorobenzoyl)benzofuran-5-yl)methanesulfonamide (4, 29.0 mg, 0.06 mmol) was dissolved in NMP (0.5 ml) and the solution was added to a pre-warmed mixture of 3-(dibutylamino)propan-1-ol (33.7 mg, 0.18 mmol) and NaOt-Bu (17.3 mg, 0.18 mmol) in NMP (0.5 ml) at about n60° C. The resulting reaction mixture was stirred at about 60° C. and the most of starting material (4) was converted by HPLC after 1.5 hours. The in-process sample at about 1.5 hour indicated target molecule (5) formation: LCMS [MH$^+$]: m/z=647.40, $t_R$=7.80 min.

IV. Conversion of Compound (5) to Compound (I)

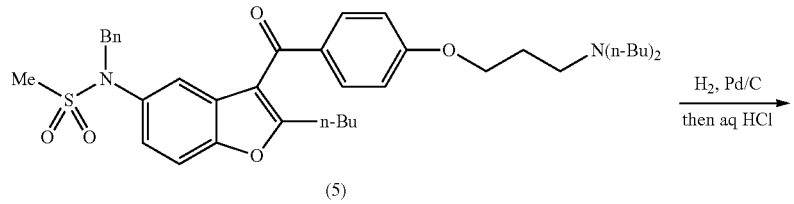

An isopropanol solution of compound (5) (1 equiv) and Pd—C (10 weight %) are agitated under a hydrogen atmosphere (20-45 psig). The catalyst is filtered, and the solution is treated with aqueous HCl (1.2 equiv). The resulting solids are isolated by filtration to afford compound (I).

V. Cu-Catalyzed Sulfonamide Coupling of Compound (3) to Provide Compound (6)

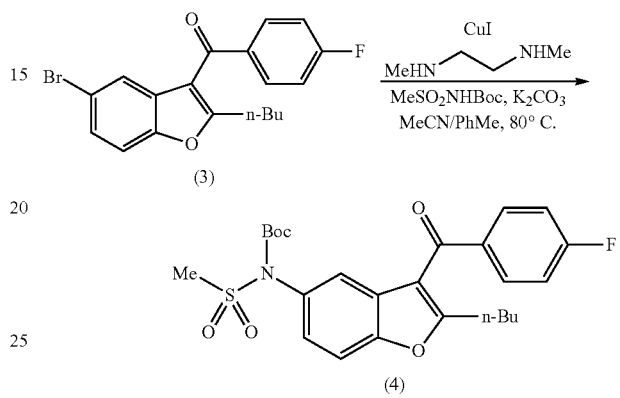

Compound (3) (1 equiv.), N-boc-methanesulfonamide (3 equiv.), K$_2$CO$_3$ (3 equiv), CuI (0.5 equiv), acetonitrile (7 volumes) and toluene (7 volumes) are combined and the resulting mixture is sparged with N$_2$. N,N'-dimethylethane-1,2-diamine (10 equiv.) is then added, and the reaction mixture is heated at about 80° C. for about 3 hours. The reaction mixture is cooled to ambient temperature and filtered through a pad of celite. The celite cake is rinsed with acetonitrile (13 volumes) and the filtrate is concentrated under reduced pressure. The residue is dissolved in isopropyl acetate (33 volumes), washed with aqueous HCl and 20% aqueous NaCl, dried over Na$_2$SO$_4$, filtered, and concentrated under reduced pressure. The crude residue is purified by chromatography on silica gel to afford compound (6).

VI. Nucleophilic Aromatic Substitution of Compound (6) to Provide Compound (7)

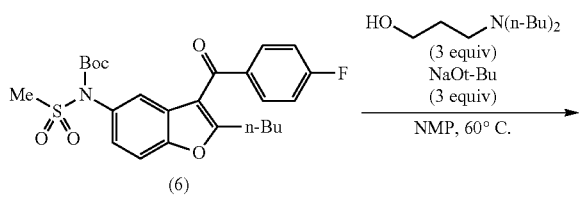

(6)

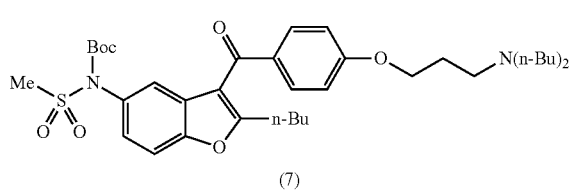

(7)

A mixture of dibutylamino propanol (3 equiv), sodium tert-butoxide (3 equiv) and NMP (10 volumes) is heated at about 60° C. under $N_2$ for about 10 minutes. A solution of compound (6) (1 equiv) in NMP (6 volumes) is added dropwise to the reaction mixture over about 3 minutes. The transfer is completed with additional NMP. The reaction mixture is heated at about 60° C. for about 25 minutes, then cooled to about 0° C. and diluted with isopropyl acetate. To the mixture is then added aqueous HCl. Following separation of the phases, the organic layer is washed with water, dried over $Na_2SO_4$, filtered and concentrated. The crude product is purified by chromatography on silica gel to afford compound (7).

VII. Conversion of Compound (7) to Compound (I)

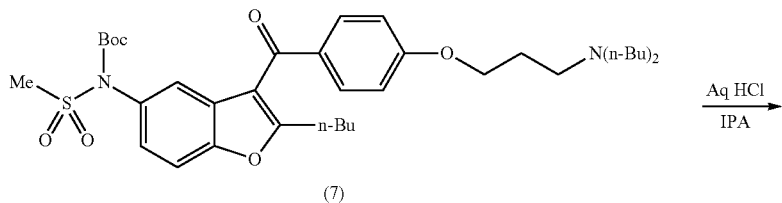

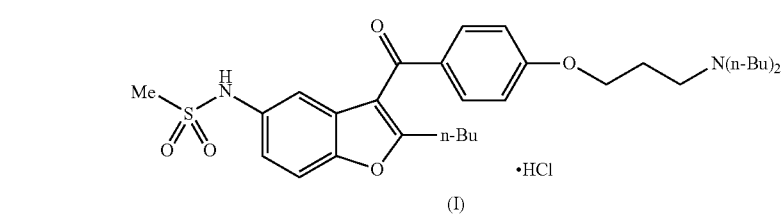

An isopropanol solution of compound (7) (1 equiv) is treated with concentrated aqueous HCl (2.2 equiv). The resulting solids are isolated by filtration to afford compound (I).

We claim:
1. A process for making dronedarone of formula

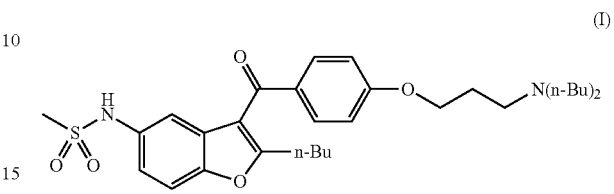

or a pharmaceutically acceptable salt thereof, comprising the steps of:
a. reacting the compound of formula (1) with the compound of formula (2) in the presence of a Lewis acid and a suitable solvent to form the compound of formula (3) as shown below:

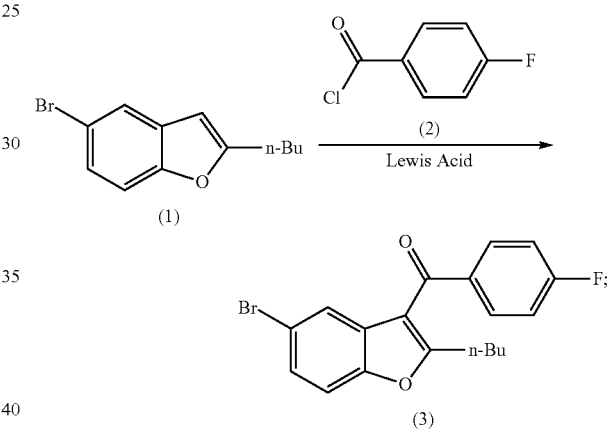

b. reacting the compound of formula (3) with N-benzyl-methanesulfonamide (MeSO$_2$NHBn) in the presence of a suitable catalyst and a suitable solvent to form the compound of formula (4) as shown below:

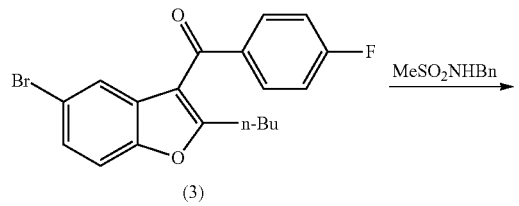

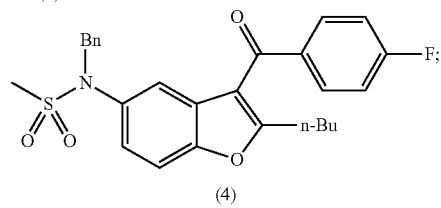

c. reacting the compound of formula (4) with dibutylaminopropanol in the presence of a suitable base and a suitable solvent to form the compound of formula (5) as shown below:

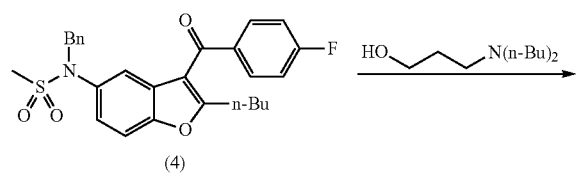

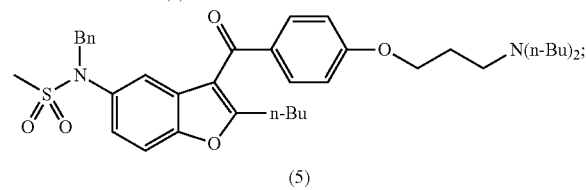

d. reacting the compound of formula (5) with a suitable deprotecting agent to form the compound of formula (I) as shown below:

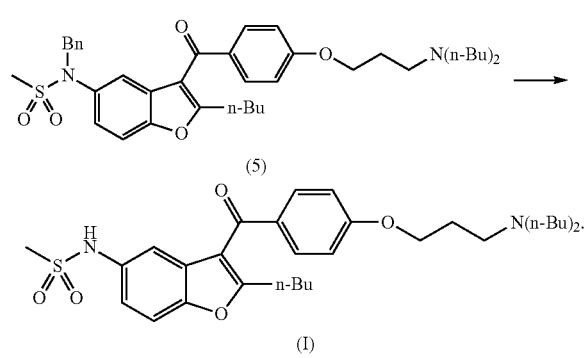

2. The process according to claim 1 wherein the reaction to prepare compound of formula (4) comprises use of Cu or palladium catalysts.

3. A process for making dronedarone acid addition salt

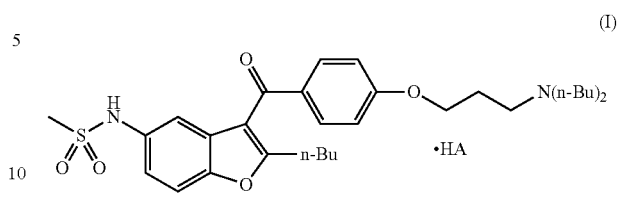

comprising the steps of:

a. reacting the compound of formula (1) with the compound of formula (2) in the presence of a Lewis acid and a suitable solvent to form the compound of formula (3) as shown below:

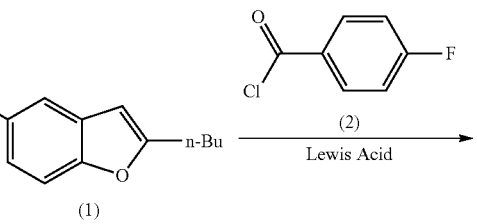

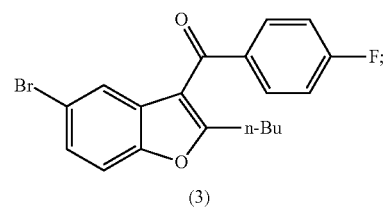

b. reacting the compound of formula (3) with N-benzyl-methanesulfonamide (CH$_3$SO$_2$NHBn) in the presence of a suitable catalyst and a suitable solvent to form the compound of formula (4) as shown below:

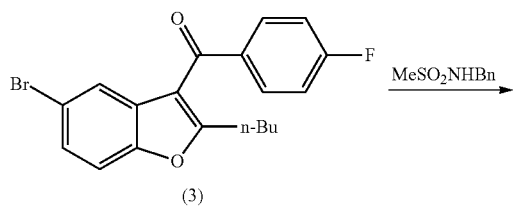

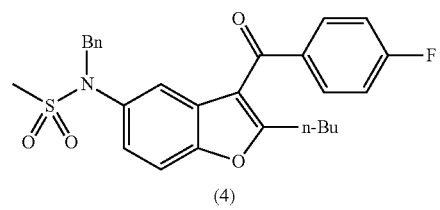

c. reacting the compound of formula (4) with dibutylaminopropanol in the presence of a suitable base and a suitable solvent to form the compound of formula (5) as shown below:

23

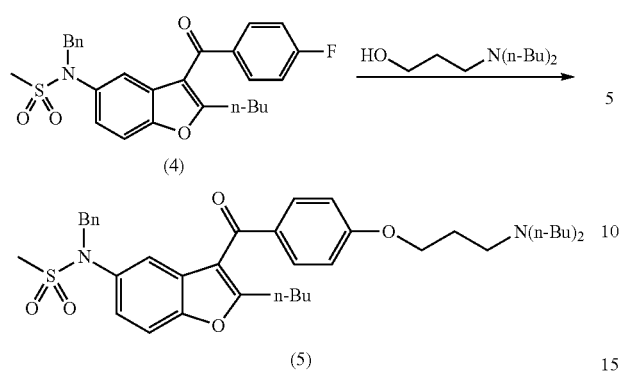

d. reacting the compound of formula (5) with a suitable deprotecting agent to form the compound of formula (I) as shown below:

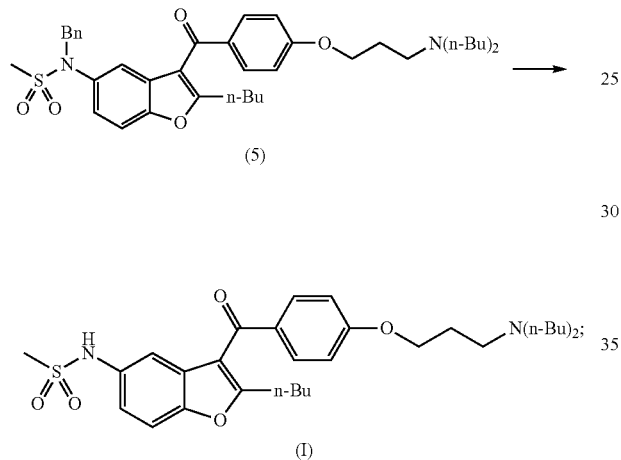

and e. reacting the compound of formula (I) with a suitable acid (HA) and a suitable solvent to afford the acid salt of the compound of formula (I) as shown below:

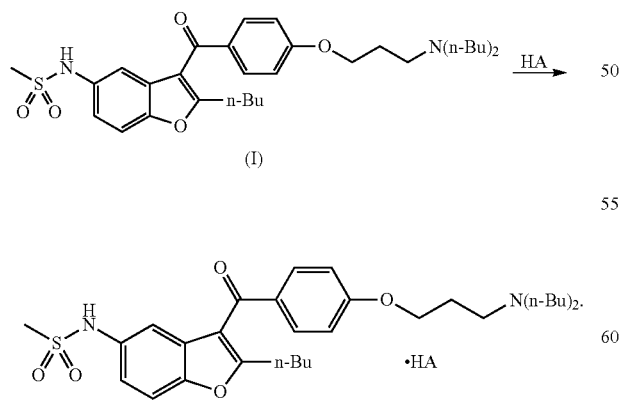

4. The process according to claim 3 wherein the reaction to prepare compound of formula (6) comprises use of Cu or palladium catalysts.

24

5. A process for making dronedarone of formula (I)

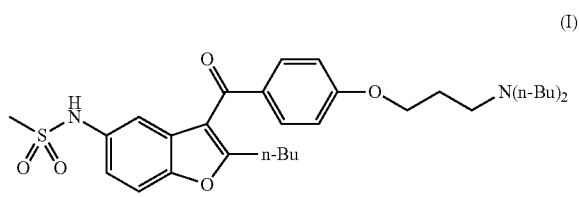

or a pharmaceutically acceptable salt thereof, comprising the steps of:

a. reacting the compound of formula (1) with the compound of formula (2) in the presence of a Lewis acid and a suitable solvent to form the compound of formula (3) as shown below

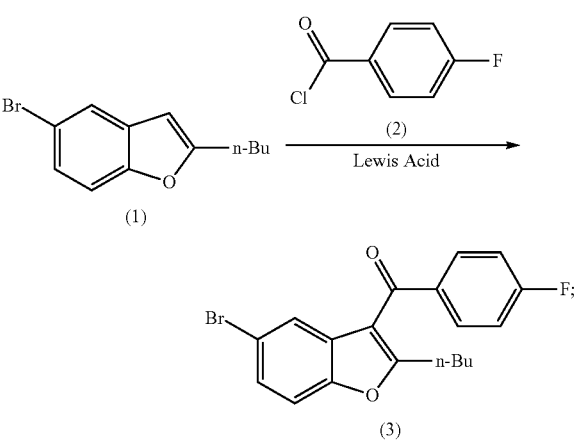

b. reacting the compound of formula (3) with Boc-protected methanesulfonamide and a suitable catalyst and a suitable solvent to afford the Boc-protected compound of formula (6) as shown below:

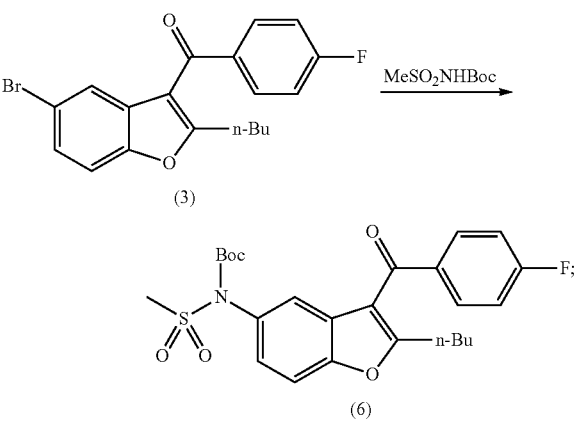

c. reacting compound of formula (6) with dibutylaminopropanol, a suitable base and a suitable solvent to afford the compound of formula (7) as shown below:

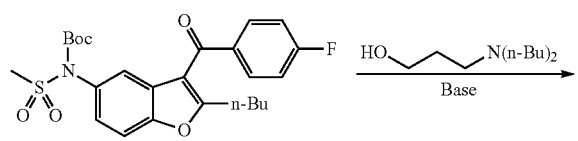
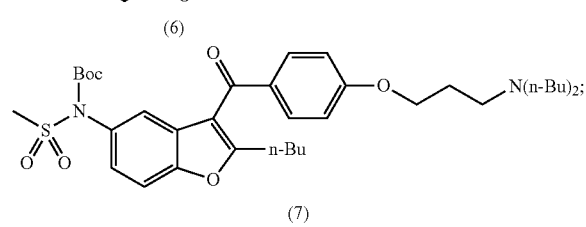
d. reacting the compound of formula (7) with a suitable add (HA) and a suitable solvent to afford the compound of formula (I) as shown below:
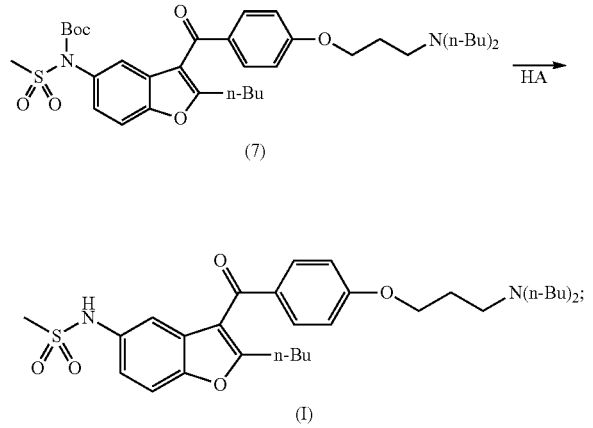
and
e. optionally reacting the compound of formula (7) with sufficient amount of a suitable add to form the add salt of the compound of formula (I) as shown below:
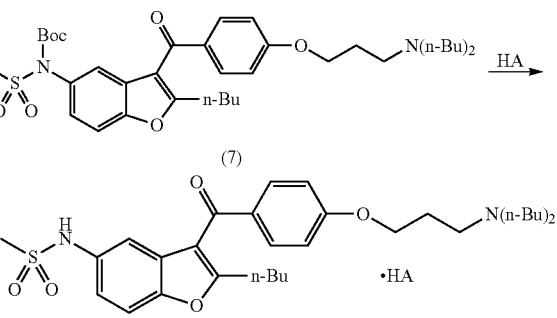
6. A compound of the formula (4) or formula (6)
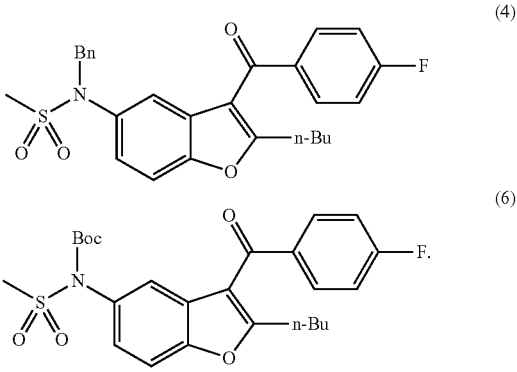
* * * * *